United States Patent
Vedachalam et al.

(10) Patent No.: US 6,624,307 B1
(45) Date of Patent: Sep. 23, 2003

(54) PROCESS FOR PRODUCING 2,6-DIHYDROXY-3,4-DIALKYLPYRIDINES

(75) Inventors: Murugappa Vedachalam, Raynham, MA (US); Jon Kirk Smith, Marion, MA (US)

(73) Assignee: ISP Investments Inc., Wilmington, DE (US)

( * ) Notice: Subject to any disclaimer, the term of this patent is extended or adjusted under 35 U.S.C. 154(b) by 2 days.

(21) Appl. No.: 10/109,434

(22) Filed: Mar. 28, 2002

(51) Int. Cl.[7] .................... C07D 213/09; C07D 213/16; C07D 213/67

(52) U.S. Cl. ....................... 546/250; 546/290

(58) Field of Search .................. 546/250, 290

(56) References Cited

U.S. PATENT DOCUMENTS

| | | | |
|---|---|---|---|
| 4,745,652 A | 5/1988 | Rose et al. ..................... | 8/409 |
| 4,838,893 A | 6/1989 | Rose et al. ..................... | 8/405 |
| 4,900,325 A | 2/1990 | Rose et al. ..................... | 8/408 |
| 5,769,903 A | 6/1998 | Audousset et al. ............ | 8/409 |
| 6,074,438 A | 6/2000 | Lim et al. ...................... | 8/409 |

OTHER PUBLICATIONS

Kenner C. Rice in the Synthesis and Analgesic . . . Journal of Medicinhl Chemistry 1975, vol 18 No. 8.*
James Kutney et in Synthesis in Pyridine Series 1961.*
J.B. Wibout and E.C. Kooyman, Synthesis of 3,4–Dimethylpyridie, 2,3–Dimethylpyridine and 2–Methyl–3–Ethylpyridine, *Rec. Trav. Chim.*, vol. 63, p. 231 (1944).
Rogerson and Thorpe, "Some Alkyl Derivatives of Glutaconic Acid and 2:6–Dihydroxypyridine", *Journal of the Chemical Society*, vol. 87, pp. 1685 (1905).

\* cited by examiner

*Primary Examiner*—Rita Desai
(74) *Attorney, Agent, or Firm*—Willliam J. Davis; Imre Balogh

(57) ABSTRACT

Commercially viable process for producing 2,6-dihydroxy-3,4-dimethlpridine. The process includes reacting 2-cyanoacetamide with sodium methoxide followed by condensation with ethyl 2-methylacetoacetate in methanol to give the sodium salt of 2,6-dihydroxy-4,5-dimethyl-3-pyridinecarbonitrile. The sodium salt of 2,6-dihydroxy-4,5-dimethyl-3-pyridinecarbonitrile is hydrolyzed with hydrobromic acid and decarboxylated to the hydrobromide salt of 2,6-dihydroxy-3,4-dimethylpyridine. The desired 2,6-dihydroxy-3,4-dimethylpyridine is produced from the hydrobromide salt by neutralizing the same with sodium hydroxide.

8 Claims, No Drawings

PROCESS FOR PRODUCING 2,6-DIHYDROXY-3,4-DIALKYLPYRIDINES

BACKGROUND OF THE INVENTION

1. Field of the Invention

This invention relates in general to a composition for the oxidation dyeing of keratin fibers, in particular human keratin fibers such as hair. More particularly, it relates to pyridine derivatives made by a novel process, which derivatives are used in such composition.

2. Reported Developments

The preferred compound of the present invention, 2,6-dihydroxy-3,4-dimethylpyridine, is known and has been reported by H. Rogerson and J. F. Thorpe, *J. Chem. Soc.*, (1905) 87, 1685 and J. P. Wibaut and E. C. Kooyman, *Rec. Trav. Chim.* (1944), 63, 231. Years later, the compound and its use in hair-dyeing composition was reported in U.S. Pat. Nos. 4,838,893, 4,900,325 and 5,769,903. The above-quoted patents do not appear to describe the synthesis of 2,6-dihydroxy-3,4-diakylpyridine which, by the literature references, appears to be economically unattractive.

SUMMARY OF THE INVENTION

Compounds of substituted 2,6-dihydroxy-3,4-dialkylpyridine are prepared by the following synthetic method shown in Scheme A:

SCHEME A

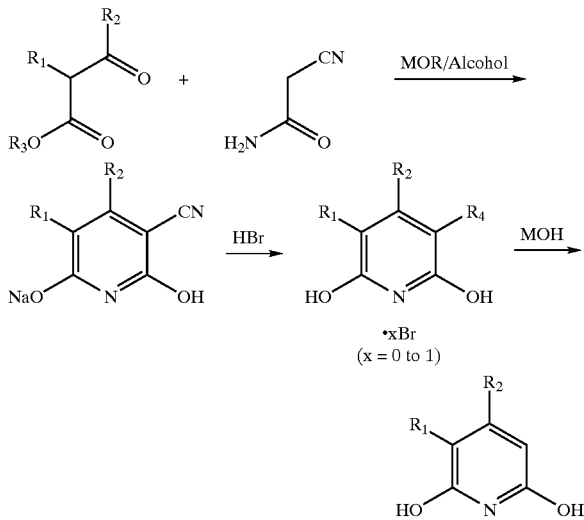

wherein
- $R_1$ is H, $C_1$–$C_4$ alkyl or aryl;
- $R_2$ is H, $C_1$–$C_4$ alkyl or aryl;
- $R_3$ is methyl, ethyl, t-butyl;
- $R_3$ is H, CN, $CONH_2$;
- M is an alkali metal, preferably Na or K;
- R is methyl, ethyl or tert-butyl; and
- Alcohol is methanol, ethanol, isopropanol, propanol, butanols or pentanols.

The preferred compound produced by the method of the present invention is 2,6-dihydroxy-3,4-dimethylpyridine is shown in Scheme B:

SCHEME B

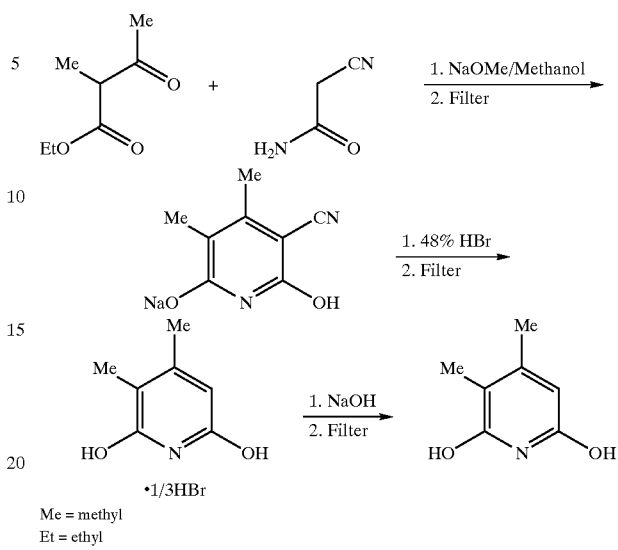

Me = methyl
Et = ethyl

DETAILED DESCRIPTION OF THE INVENTION

It has been reported that 2,6-dihydroxy-3,4-dialkylpyridine is useful as a coupling agent in oxidative hair dyeing. The compound can be made by a lengthy procedure shown in Scheme I as reported by J. P. Wibaut and E. C. Kooyman, *Rec. Trav. Chim.* (1944), 63, 231.

SCHEME I

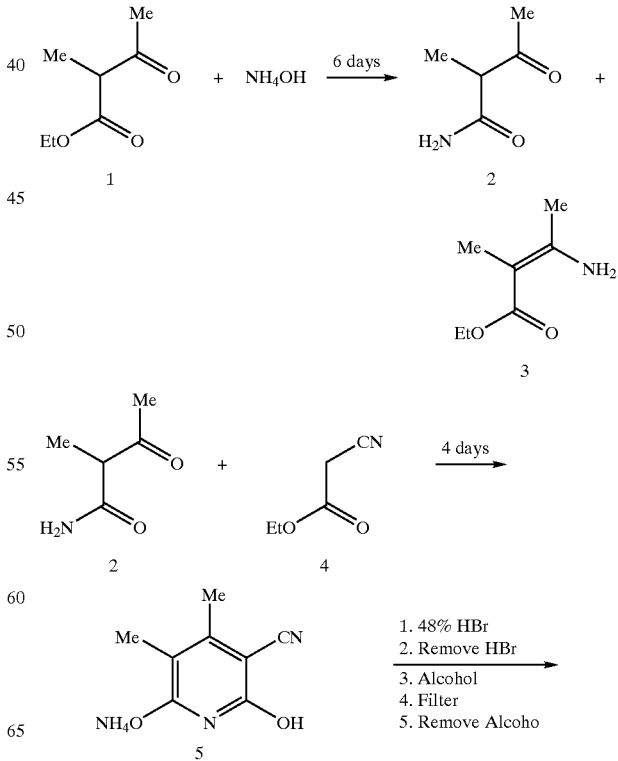

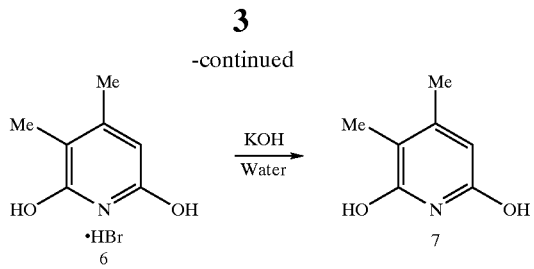

2-methylacetoacetamide 2, made from ethyl 2-methylacetoacetate 1 by reaction with ammonium hydroxide for six days (at about 60% yield), is reacted with ethyl cyanoacetate 4 over four days to produce 2,6-dihydroxy-4,5-dimethyl-3-pyridinecarbonitrile, ammonium salt 5 (90% yield). The ammonium salt is hydrolyzed with hydrobromic acid and decarboxylated. The excess hydrobromic acid is evaporated to dryness followed by filtration of ammonium bromide after taking up the 2,6-dihydroxy-3,4-dimethylpyridine hydrobromide salt 6 in absolute ethyl alcohol. The ethyl alcohol is evaporated to dryness and the residue is heated with water and potassium hydroxide to isolate 2,6-dihydroxy-3,4-dimethylpyridine (70% yield).

It has also been reported by H. Rogerson and J. F. Thorpe, *J. Chem. Soc.* (1905) 87, 1685, that 2,6-dihydroxy-3,4-dimethylpyridine can be made from ethyl α-cyano-βγ-dimetkylglutaconate 9, made from condensation of ethyl cyanoacetate with ethyl 2-methylacetoacetate, by alkali hydrolysis/cyclization. It also involves a lengthy and cumbersome workup procedure as shown in Scheme II.

SCHEME II

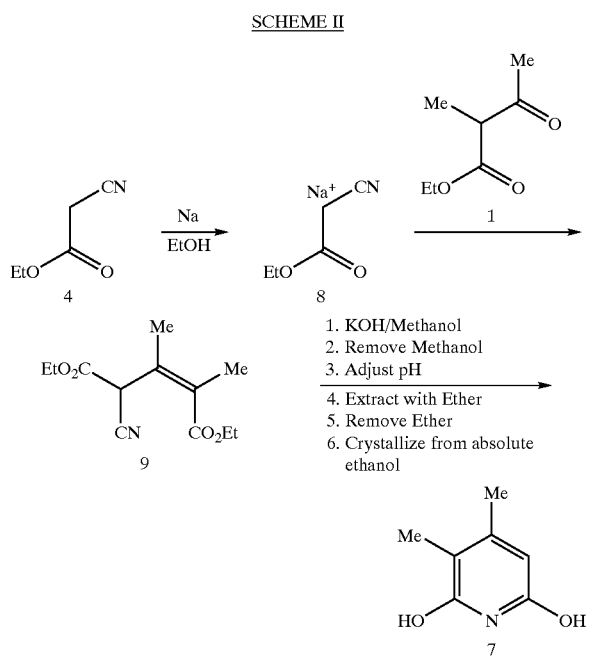

Neither of the above-described two methods for making 2,6-dihydroxy-3,4-dimethylpyridine is attractive commercially since they are lengthy and cumbersome. For this reason an alternate procedure constituting the present invention was developed to produce the compound at commercial volumes at low cost and minimum waste. Scheme B shows the preparation of 2,6-dihydroxy-3,4-dimethylpyridine accompanied with comments and comparison with the prior art.

SCHEME B

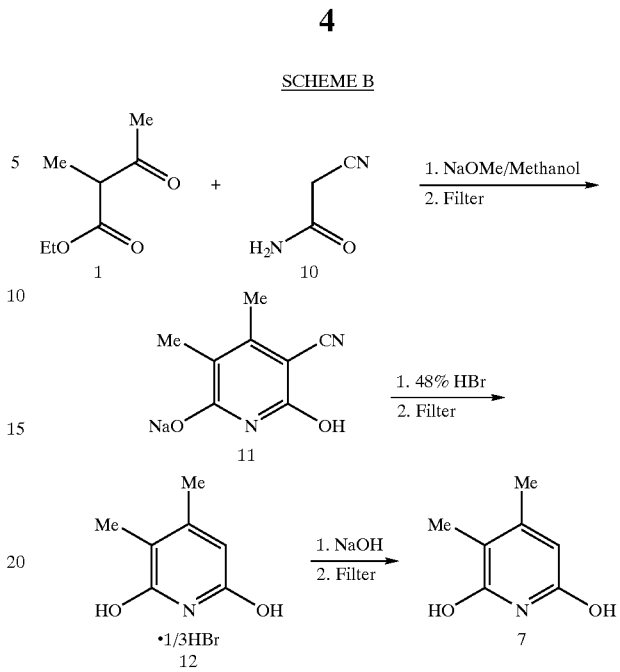

The sodium salt of 2-cyanoacetamide is generated in situ from 2-cyanoacetamide and 25% sodium methoxide in methanol. The sodium salt is reacted with ethyl 2-methylacetoacetate. The reaction is monitored for the consumption of ethyl 2-methylacetoacetate by a GC method. At the end of the reaction, 2,6-dihydroxy-4,5-dimethyl-3-pyridinecarbonitrile, sodium salt 1 is filtered off. In comparison, the prior art process shown in Scheme I, describes a very long cycle time preparation of the corresponding ammonium salt. The 2-methylacetoacetamide 2 is prepared from ethyl 2-methylacetoacetate by shaking with ammonium hydroxide for a lengthy six days and at a loss of 40% ethyl 2-methylacetoacetate towards the side product ethyl 3-amino-2-methylcrotonate 3. The 2-methylacetoacetamide is reacted with ethyl 2-cyanoacetate for a long four day period.

In the present invention, the sodium salt 11 is reacted with 48% hydrobromic acid and the crystallized 2,6-dihydroxy-3,4idmethylpyridinium hydrobromide salt 12 is simply filtered off at the end of the reaction. The water-wet hydrobromide salt 12 is mixed back with water and the pH adjusted using 50% sodium hydroxide and the product is filtered off. The prior art however, shown in Scheme I, describes that the corresponding ammonium salt is reacted with 48% hydrobromic acid. At the end of the removal of the cyano group by hydrolysis and decarboxylation, a very tedious removal of the hazardous excess hydrobromic acid by distillation to dryness, which is impractical at large commercial scales, then the residue is taken up in absolute alcohol. The insoluble bromide is then filtered off. The alcohol is removed by distillation to dryness, which again is impractical at commercial scales, and the residue containing 2,6-dihydroxy-3,4-dimethylpyridinium hydrobromide salt is boiled with potassium hydroxide to give 2,6-dihydroxy-3,4-dimethylpyridine. The overall yield of the prior art, in addition to being lengthy and cumbersome, yielded 38% of the product. The present invention yields about 51% of the product and is safe, fast and economical.

For preparing the essential components used in the process of the present invention, the following examples are provided re. compounds 11, 12 and 7 identified in Scheme B.

Example 1

2,6-Dihydroxy-4,5-Dimethyl-3-Pyridinecarbonitrile, Sodium Salt 11

To a slurry of 2-cyanoacetamide (117.71 g, 1.46 moles) in methanol (900 mL) is added 25% sodium methoxide (315.12 g, 1.46 moles) at 0–10° C. over a period of 45 min. Initial thick slurry goes into a thin slurry and becomes a thick slurry. The slurry is mixed at 10° C. for 1 h. Ethyl 2-methylacetoacetate (201.84 g, 1.4 moles) is added to the slurry at 10–15° C. over a period of 1 h 30 min. The slurry is mixed at 10–15° C. for 1 h and 60–65° C. for 15–20 h. The mixture is cooled to 20° C. and mixed at 20° C. for 1 h. The solid is filtered and washed with methanol. The wet cake is dried at 40° C./vacuum to give 233.1 g of the sodium salt 11 (89% yield). IR (Neat): 2187, 1644, 1596, 1382, 885 $cm^{-1}$. mp<300° C.; $^1$HNMR (DMSO-$d_6$, 400 MHz): $\delta$1.70(s, 3H, $CH_3$), 1.97(s,3H, $CH_3$), 9.37(s,1H, OH); $^{13}$CNMR(DMSO-$d_6$, 400 MHz): $\delta$10.25, 17.75, 79.20, 107.48, 121.27, 153.50, 164.36, 164.93; Sodium metal (ICP-AE)=13.0%.

Example 2

2,6Dihydroxy-3,4-Dimethylpyridine, ⅓ Hydrobromide 12

To sodium salt 11 (225 g, 1.2 moles) is added 48% hydrobromic acid (850 mL) at 20–25° C. No apparent exotherm is present. The slurry is slowly and cautiously heated to 120–125° C. over a period of 1 h. It becomes a homogeneous solution and is held at 120–125° C. for 24 h. The mixture is allowed to cool down to 20° C. over 3–4 h. The crystallized solid is filtered, washed with water to give 2,6-dihydroxy-3,4-dimethylpyridine, ⅓ HBr 12 [146.8 g; volatiles=15.7%; 64.5% yield; Bromide (titration)=12.2%]. mp 135–165° C.; IR(Neat): 1619, 1577, 1534, 1297, 892 $cm^{-1}$, $^1$HNMR ($CF_3COOD$, 400MHz); $\delta$2.37(s, 3H, $CH_3$), 2.60(s, 3H, $CH_3$), 6.83(s, 1H, aromatic); $^{13}$CNMR ($CF_3COOD$, 400 MHz): $\delta$11.25, 22.39(d), 106.38, 114.86, 156.59(d), 166.87(d).

Example 3

2,6-Dihydroxy-3,4-Dimethylpyridine 7

The wet hydrobromide salt 12 (113.8 g in 135 g) is mixed with water (400 mL) and the pH is adjusted to 5.2 with 50% NaOH (25.8 g). The solid is filtered, washed with water and methanol. The wet product is dried at 60° C. under vacuum to give 2,6-dihydroxy-3,4-dimethylpyridine 3,4-dimethylpyridine 7 as off-white to tan powder (87.71g, 88.3% yield. mp 185–187° C. (lit. mp 187° C.) IR(Neat): 1621, 1600, 1535, 1301, 894, $cm^{-1}$. $^1$HNMR ($CF_3COOD$, 400 MHz); $\delta$2.20(s, 3H, $CH_3$), 2.44(s, 3H, $CH_3$), 6.60(s, 1H, aromatic); $^{13}$CNMR ($CF_3COOD$, 400 MHz): $\delta$11.04, 22.02 (d), 105.97, 114.53, 156.66(d), 166.55(d).

Brief Comparison and Advantages of the Present Invention Over the Prior Art

The present invention uses ethyl 2-methylacetoacetate, 2-cyanoacetamide and sodium methoxide for making the sodium salt of 2,6-dihydroxy-4,5-dimethyl-3-pyridincarbonitrile in 89% yield. The prior art uses ethyl 2-methylacetoacetate to make 2-methylacetoacetamide and reacts that further with ethyl 2-cyanoacetate for making the ammonium salt of 2,6-dihydroxy-4,5-dimethyl-3-pyridinecarbonitrile in 54% yield, and produces a large amount of the side product aminocrotonate 3.

In making 2,6-dihydroxy-4,5-dimethylpyridine, the present invention uses a sodium salt of 2,6-dihydroxy-4,5-dimethyl-3-pyridinecarbonitrile, whereas the prior art uses an ammonium salt.

In the present invention, the 2,6-dihydroxy-4,5-dimethylpyridine is isolated as its hydrobromide salt by simple filtration, whereas in the prior art it is isolated by a series of tedious extraction, filtration and evaporation processes.

As shown in Scheme A in the Summary of the Invention, various substituted 2,6-dihydroxy-3,4-dialkylpyridines can be made, the scheme being reproduced herein. The analogous compounds in Scheme A and the procedural steps are denoted by the numerals used in Scheme B.

SCHEME A

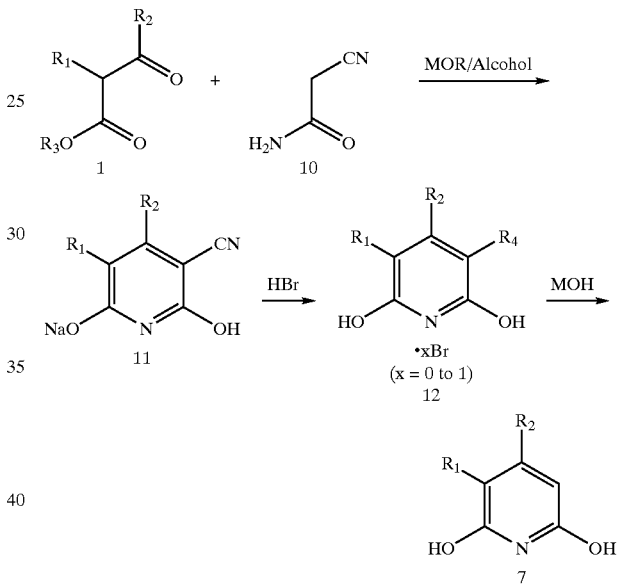

wherein $R_1$ is H, $C_1$–$C_4$ alkyl or aryl;

$R_2$ is H, $C_1$–$C_4$ alkyl or aryl;

$R_3$ is methyl, ethyl, t-butyl;

$R_4$ is H, CN, $CONH_2$;

M is an alkali metal, preferably Na or K;

R is methyl, ethyl or tert-butyl; and

Alcohol is methanol, ethanol, isopropanol, propanol, butanols or pentanols.

Having described the invention, it will be apparent to those skilled in the art that various changes and modifications may be made thereto. It is intended to include such changes and modification limited only by the scope of the appended claims.

What is claimed is:

1. A process for the production of 2,6-dihydroxy-3,4-dialkylpyridine having the formula

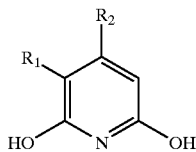

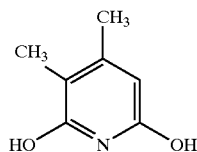

wherein $R_1$ and $R_2$ are independently H, $C_1$–$C_4$ alkyl or aryl, comprising the steps of:

reacting 2-cyanoacetamide in alcohol with alkali metal methoxide to produce a slurry;

adding with mixing ethyl 2-alkylacetoacetate to the slurry;

filtering the slurry and washing the filtrate with alcohol to obtain the sodium salt of 2,6-dihydroxy-4,5-dialkyl-3-pyridinecarbonitrile;

adding hydrobromic acid to the sodium salt of 2,6-dihydroxy-4,5-dialkyl-3-pyridinecarbonitrile to obtain a homogeneous solution;

cooling the solution to obtain a crystallized solid of 2,6-dihydroxy-3,4-diakylpyridine hydrobromide salt; and washing the crystallized solid of 2,6-dihydroxy-3,4-dialkylpyridine hydrobromide salt with an alkali, water and alcohol to obtain the 2,6-dihydroxy-3,4-dialkylpyridine.

2. The process of claim 1 wherein $R_1$ and $R_2$ are independently methyl.

3. The process of claim 1 wherein said alkali metal methoxide is sodium methoxide.

4. The process of claim 1 wherein 2-cyanoacetamide is reacted with alkali metal methoxide in methanol.

5. The process of claim 1 wherein said sodium salt of 2,6-dihydroxy-4,5-dialkyl-3-pyridinecarbonitrile is the sodium salt of 2,6-dihydroxy-4,5-dimethyl-3-pyridinecarbonitrile.

6. The process of claim 1 wherein said crystallized solid of 2,6-dihydroxy-4,5-dialkylpyridine hydrobromide salt is filtered and washed with water and methanol.

7. The process of claim 1 wherein said hydrobromide salt is mixed with water and the pH thereof is adjusted to about 5.2 with sodium hydroxide.

8. A process for the production of 2,6-dihydroxy-3,4-dimethylpyridine having the formula comprising the steps of:
reacting 2-cyanoacetamide of the formula

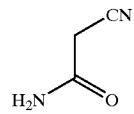

in methanol with sodium methoxide to produce a slurry;
adding, with mixing, ethyl 2-methylacetoacetate having the formula

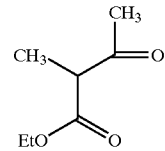

to the slurry;
filtering the slurry and washing the filtrate with methanol to obtain the sodium salt of 2,6-dihydroxy-4,5-dimethyl-3-pyridinecarbonitrile;

adding 48% of hydrobromic acid to the sodium salt of 2,6-dihydroxy-4,5-dimethyl-3-pyridinecarbonitrile and heating to about 120°–125° C. to obtain a homogenous solution;

cooling the solution to obtain a crystallized solid of 2,6-dihydroxy-3,4-dimethylpyridine hydrobromide salt;

filtering the crystallized solid and washing with water to obtain a wet hydrobromide salt;

mixing the hydrobromide salt with water and adjusting the pH to about 5.2 with 50% sodium hydroxide;

filtering the mixture and washing with water and methanol to obtain a wet-cake; and drying the wet-cake to obtain 2,6-dihydroxy-3,4-dimethylpyridine as an off-white to tan powder.

* * * * *